United States Patent
Leggett et al.

(10) Patent No.: US 10,520,433 B2
(45) Date of Patent: Dec. 31, 2019

(54) TURBIDIMETER

(71) Applicant: Hach Company, Loveland, CO (US)

(72) Inventors: Richard Edward Leggett, Dickinson, TX (US); Wayne Boris Perdue, Berlin (DE); Andreas Mitreiter, Berlin (DE)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 16/368,503

(22) Filed: Mar. 28, 2019

(65) Prior Publication Data

US 2019/0219502 A1   Jul. 18, 2019

Related U.S. Application Data

(62) Division of application No. 15/512,408, filed as application No. PCT/US2015/050993 on Sep. 18, 2015, now Pat. No. 10,281,393.

(Continued)

(51) Int. Cl.
*G01N 21/51* (2006.01)
*G01N 21/47* (2006.01)

(52) U.S. Cl.
CPC ..... *G01N 21/51* (2013.01); *G01N 2021/4726* (2013.01)

(58) Field of Classification Search
CPC ...... G01J 3/0205; G01J 3/0291; G01J 3/0256; G01J 3/0272; G01J 3/10; G01J 3/0216; G01J 3/0264; G01J 3/0208; G01J 3/2803; G01J 5/10; G01J 2003/2806; G01J 3/0275; G01J 3/027; G01J 3/0289; G01J 3/36; G01J 2003/102; G01J 2003/104; G01J 2003/1213; G01J 2003/1217; G01J 2003/2866; G01J 3/0202; G01J 3/021; G01J 3/0229; G01J 3/0259; G01J 3/0286;
(Continued)

(56) References Cited

U.S. PATENT DOCUMENTS 3,826,574 A * 7/1974 Brown, Jr. ............. G01N 21/51
356/339
4,710,642 A    12/1987 McNeil
(Continued)

FOREIGN PATENT DOCUMENTS

WO    WO2015043675 A1    4/2015

OTHER PUBLICATIONS

European Patent Office, International Search Report, dated Nov. 25, 2015, 2 pages, European Patent Office, Rijswijk, The Netherlands.
(Continued)

*Primary Examiner* — Michael P Stafira
(74) *Attorney, Agent, or Firm* — Ference & Associates LLC

(57) ABSTRACT

Various turbidimeters are described that can detect light directly in a substantially circular, e.g., encompassing, manner such that an increased amount of scattered light from a sample vial may be detected by a light detector, e.g., a photodiode or photodiode array. In an embodiment, a substantially circular photodiode array is provided to directly detect scattered light in an arc about the sample vial. In other embodiments, light guides are provided in an arc element that guides light to a detector or detectors. Other aspects are described and claimed.

7 Claims, 5 Drawing Sheets

Related U.S. Application Data

(60) Provisional application No. 62/052,916, filed on Sep. 19, 2014.

(58) Field of Classification Search
CPC .... G01J 3/0297; G01J 3/26; G01J 3/28; G01J 3/42; G01J 5/0846; G01N 2201/0221; G01N 21/255; G01N 21/31; G01N 2201/0627; G01N 21/65; G01N 2001/4088; G01N 2021/0118; G01N 2021/6417; G01N 21/33; G01N 21/359; G01N 21/53; G01N 21/532; G01N 21/6452; G01N 2201/062; G01N 2201/0634; G01N 2201/0691; G01N 33/1886; G01N 15/1404; G01N 15/1436; G01N 1/4077; G01N 2021/152; G01N 2021/6463; G01N 2021/6471; G01N 2021/6482; G01N 21/01; G01N 21/05; G01N 21/15; G01N 21/17; G01N 21/27; G01N 21/3151; G01N 21/35; G01N 21/3563; G01N 21/474; G01N 21/51; G01N 21/6428; G01N 2201/021; G01N 2201/06113; G01N 2201/0625; G01N 2201/0633; G01N 2201/0636; G01N 2201/064; G01N 2201/0642; G01N 2201/0668; G01N 2201/08; G01N 2201/121; G01N 27/02; G01N 27/026; G01N 27/283; G01N 33/02; G01N 33/025; G01N 33/18; G01N 33/493
See application file for complete search history.

(56) References Cited

U.S. PATENT DOCUMENTS

| | | |
|---|---|---|
| 5,140,168 A | 8/1992 | King |
| 6,606,157 B1 | 8/2003 | Kaye et al. |
| 7,046,347 B1 * | 5/2006 | Amend ............... G01N 21/31 356/338 |
| 2005/0083524 A1 | 4/2005 | Totoki |
| 2010/0020323 A1 | 1/2010 | Moosmuller et al. |

OTHER PUBLICATIONS

Bartholdi, M. et al, "Differential light scattering photometer for rapid analysis of single particles in flow", Applied Optics, May 15, 1980, 9 pages, vol. 19, No. 10, Optical Society of America.

* cited by examiner

TURBIDIMETER

CROSS REFERENCE TO RELATED APPLICATION

This application is a divisional application of co-pending U.S. application Ser. No. 15/512,408, filed on Mar. 17, 2017, and entitled "TURBIDIMETER," which in turn is a National Phase Application of International PCT Application Serial No. PCT/US15/50993, filed Sep. 18, 2015, and entitled "TURBIDIMETER", which in turn claims priority to U.S. Provisional Application Ser. No. 62/052,916, filed Sep. 19, 2014, and entitled "TURBIDIMETER", the contents of each of these prior applications are hereby incorporated by reference as if set forth in their entirety.

FIELD

The subject matter described herein relates to a turbidimeter for measuring turbidity of a liquid sample. More specifically, embodiments are directed to a novel detector that more efficiently captures radiation scattered from particles dispersed in a sample solution by taking advantage of a circular design.

BACKGROUND

A turbidimeter measures the turbidity of a liquid sample in a sample cuvette or vial. A nephelometric turbidimeter determines the concentration of solid particles suspended in a liquid sample within a sample cuvette by projecting a light beam into the liquid sample within the cuvette. A light detector detects the amount of light scattered by the suspended solid particles in a cone of solid angle, e.g., of 30° centered at 90° to the light beam axis.

If the light detector of a turbidimeter detects light scattered in one single sector of the circumference (of the cuvette, vial or sample vessel), the signal of the light detector is relatively low because much scattered light is being thrown away. Circular mirrors and/or prism arrangements have been designed to coaxially surround the liquid sample cuvette in an effort to direct radially scattered light (over the complete) circumference to the light detector. Such designs generally are acknowledged to increase the signal to noise ratio (SNR). However, many of these devices are sensitive to geometrical inaccuracies of their optical arrangements (directing the scattered light toward the light detector) and may be sensitive to non-homogenous samples (turbidity differences in the liquid sample).

BRIEF SUMMARY

In summary, an embodiment provides a turbidimeter comprising: a cone-shaped collector; the cone-shaped collector having a collar for receiving a cuvette; the collar including a light entryway that encircles the cuvette such that scattered light from the cuvette will enter the collar; a base end of the cone-shaped collector; and a detector element adjacent to the base end; the cone shaped collector comprising surfaces that form an internal light path that internally reflects the scattered light along a periphery of the cone-shaped collector from the cuvette to the base where the detector element sits.

Another embodiment provides a turbidimeter, comprising: an arc element having an arc surface and one or more connected light guides, said arc surface substantially encircling a suspended sample and being centered at ninety degrees relative to the incident light beam axis such that said arc surface gathers said scattered light from particles in the sample and transmits said scattered light through said at least one light guide to at least one photodiode detector.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
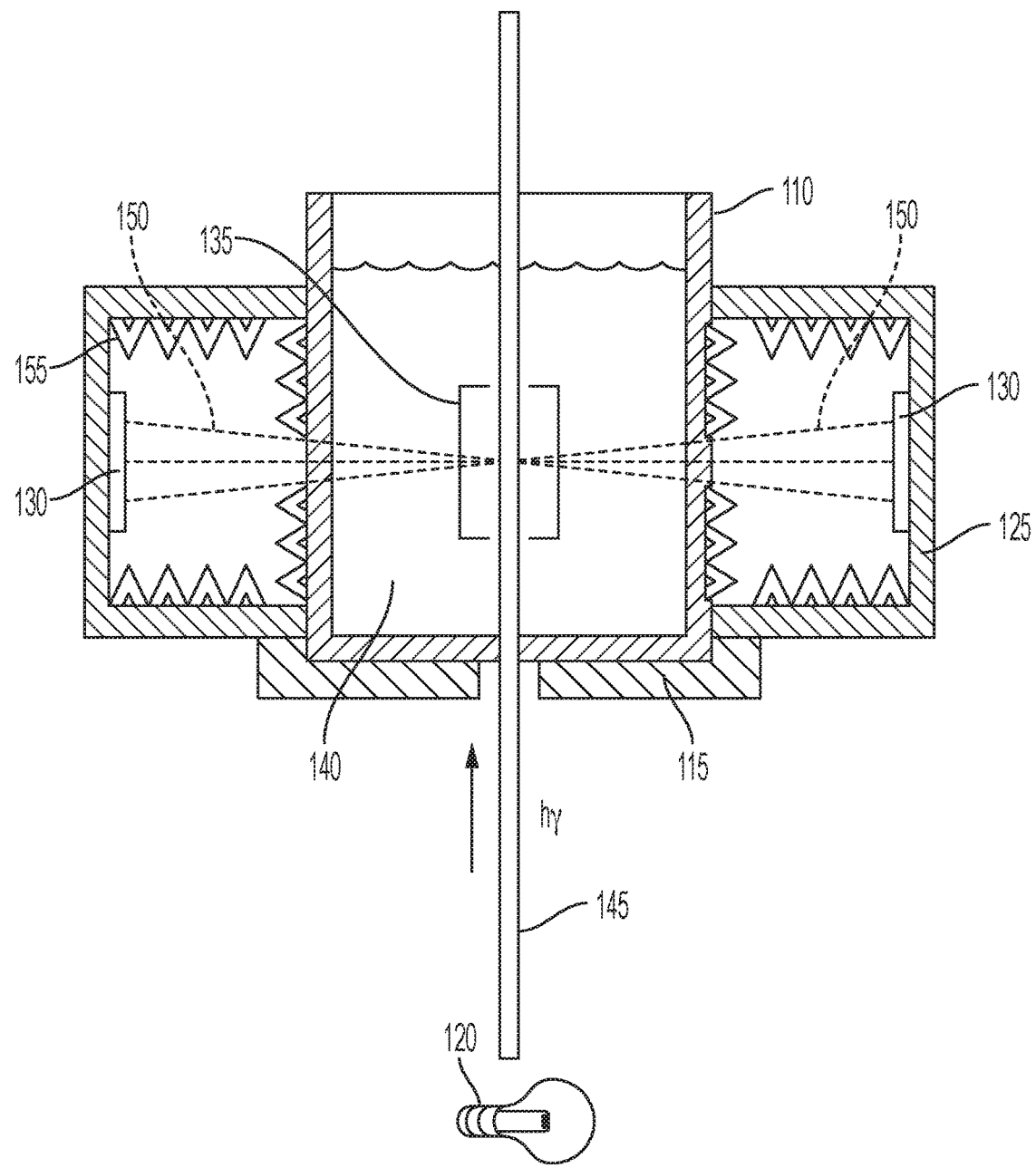
FIG. 1 illustrates an example turbidimeter.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of example embodiments. One skilled in the relevant art will recognize, however, that various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The various embodiments described herein provide turbidimeters that detect light from an arc surrounding or substantially surrounding a sample vessel or cuvette. The embodiments permit such light detection without using complex light focusing geometries. Rather, embodiments provide mechanisms to directly detect light in an arc surrounding or substantially surrounding the sample vessel or cuvette. In other embodiments, light from an arc surrounding or substantially surrounding the sample vessel or cuvette is piped or redirected to a light detector.

An embodiment provides a nephelometric turbidimeter detector comprising a 360 degree element having a plurality of contiguous photodiode arrays capable of detecting radiation from about 190 nm to about 1100 nm and arranged to capture scattered radiation at a 90 degree angle +/− about 15 degrees relative to the light beam axis. Another embodiment comprises a detector including a 360 degree element having single flexible photodiode array that detects radiation from about 190 nm to about 1100 nm and that is arranged to capture scattered radiation at a 90 degree angle +/−15 degrees relative to the light beam axis. In the various embodiments forming nephelometric turbidimeter, these embodiments may include all of the standard elements, some of which are not described.

The illustrated example embodiments will be best understood by reference to the figures. The following description is intended only by way of example, and simply illustrates certain example embodiments.

FIG. 1 depicts a cross section of a first example embodiment of the 360 degree turbidimeter detector apparatus. The example turbidimeter illustrated in FIG. 1 is substantially round when viewed from above or below. Vial 110 is a vial for holding sample solutions, e.g. water (waste water, drinking water, etc.). The vial (also referred to as a cuvette) 110 may be made from an optically clear material such as glass or quartz that is substantially transparent to radiation used to interrogate the sample, such as 660 nm, 860 nm or 880 nm radiation. The vial 110 may be configured as a cylinder, although sample vials may take any shape appropriate for the task. The vial 110 is supported by a vial holder 115 which itself is supported by a turbidimeter supporting skeleton (not shown in FIG. 1).

In operation the vial 110 sits in vial holder 115 so that the vial is held stably. The vial holder 115 abuts detector housing 125, which may be a generally circular shape and surround at least a portion of the mid-section of vial 110. The inside of detector housing 125 may be lined with light-absorbing material 155 which acts as a light baffle to absorb stray radiation that may emanate from vial 110 when illuminated. The light absorbing material 155 may also be placed in additional areas, e.g., along the length dimension of the vial to restrict light entry to a predetermined angular range. A non-limiting example light absorbing material is VANTABLACK of Surrey Nanosystems, UK.

The detector housing 125 also may act as the supporting structure for light detectors, e.g., photodiodes 130, which capture the scattered radiation from sample liquid 140. The photodiodes 130 in the example of FIG. 1 are placed contiguously in a circle on the inside of detector housing 125 so that they make up a substantially continuous array of detectors that correspond to scattered radiation along a predefined arc of scattered radiation, shown as rays 150 emanating from collected volume 135.

A light source 120 may be a broad-band visible light source, a laser, or a light emitting diode (LED). The light source 120 is selected according to the specific needs of the application and may also be used in combination with filters for selecting specific wavelengths. Typical wavelengths for turbidimeters are 660 nm and 880 nm, although these are non-limiting examples, e.g., 860 nm +/−30 nm may be used.

The light source 120 may be provided through a slit or other optical element that results in a substantially collimated light beam 145 that impinges upon the clear vial bottom, thereby passing through vial 110 and sample liquid 140 to create an illuminated volume of sample liquid termed the collected volume 135, shown by brackets in FIG. 1.

Particles which are in collected volume 135 will be illuminated, thereby acting to scatter the light randomly but on average over 360 degrees. The collected scattered light will resemble a disk of light that is thicker at its edges than its middle. The scattered light will fall upon the photodiodes 30 arrayed along the interior of detector housing 125 and thereby cause a signal to be emitted from the photodiodes 130 that is proportional to the amount of scattered light, which in turn is proportional to the amount of turbidity (e.g., NTUs).

Figure 2:
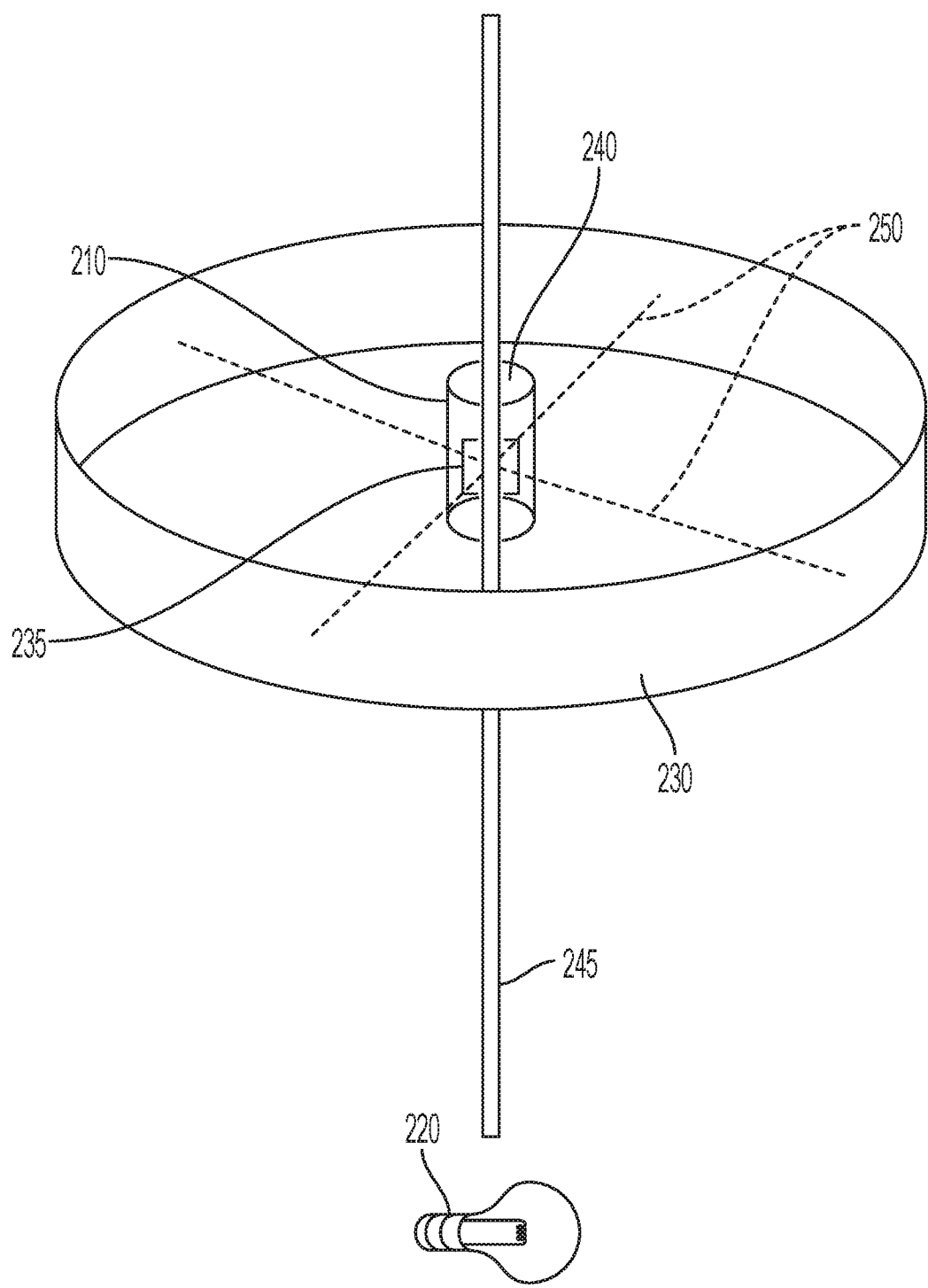
FIG. 2 illustrates another example turbidimeter.

A second example embodiment is shown in FIG. 2, which is an elevational view of a 360 degree turbidimeter detector having a circular photodiode array (PDA) 230 arranged in a substantially circular manner around the vial 210. As before, vial 210 is irradiated by collimated light beam 245, thereby causing the scattering of light 250 from collected volume 235.

Scattered light 250 impinges upon the inner surface of circular PDA 230 thereby generating a signal proportional to the number of particles scattering light in the collected volume 235. A circular PDA may be formed by film-based organic photodiodes. However, other materials may be used, including other flexible photodiode materials or an array of photodiodes configured in separate components forming a substantially circular arc or array of detectors.

The example embodiment shown in FIG. 2 is a relatively narrow band or strip of PDA film 230 that is looped around the vial's 210 equator and is designed to capture a predefined vertical slice or portion of the available scattered radiation. In FIG. 2, stray light management is not explicitly illustrated. In theory the sensitivity of the detector system may be tuned simply by changing the arc range of the flexible PDA 230. The flexible photodiodes 230 may be configured in almost limitless orientations to take advantage of the specific directions of the omni-directional scattering of the scattered light 250. For example, a diode array made addressable in the direction and subtended angle from which the light is being detected can be changed, giving the advantage that the turbidimeter may detect turbidity from samples with different physical characteristics. As will be appreciated, as with the example illustrated in FIG. 1, the arrangement of the detector(s) utilized may vary based on a variety of factors, e.g., the input light angle, the type of cuvette or sample vessel utilized, etc.

Figure 3:
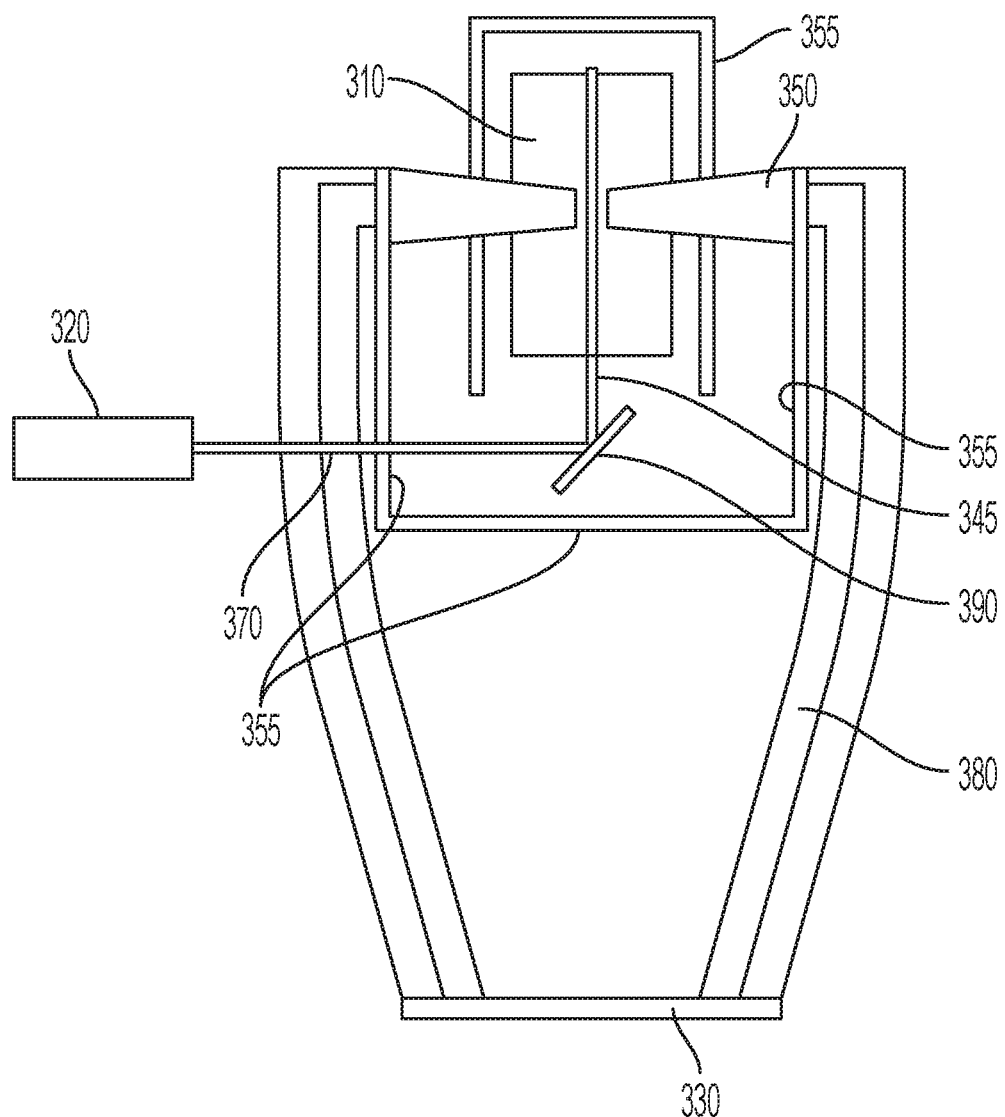
FIG. 3 illustrates another example turbidimeter.

FIG. 3 illustrates a third embodiment. In this embodiment, the turbidimeter includes an arc that is substantially circular about a mid point or portion of the sample vial 310. Here, the arc captures the scattered light 350 and directs it to a light pipe or guide material 380. In an embodiment, the light guide or pipe material 380 may be fiber optics or another suitable waveguide, e.g., a light tube such as ALTAFUOR 350 available from Altaflo.

The fiber optic or waveguide 380 may start at the surface of the arc, where the flexible PDA is arranged, e.g., in the example embodiment illustrated in FIG. 2. From there the waveguide 308 may curve about 180 degrees and meet up with all of the other waveguides, which ultimately provide the light to a single photodiode or an array thereof, e.g., as arranged in the example of FIG. 3 at 330.

Thus, incoming light 345 (e.g., infrared) from a light source is provided entryway 370 through (or around) the light pipe 380 and provides light to a sample, which may be redirected, e.g., by a mirror 309. In an embodiment, the vial may be angled to prevent reflected light from damaging the source. This light penetrates the liquid sample in the sample vial 310 and particles in the liquid sample produce scattered light, a relevant portion thereof 350 being illustrated in FIG. 3. The sample vial 301 may be housed in a manner, e.g., by light blockers 355 as shown in FIG. 3 (which may in turn include a light absorbing material, e.g., as described in connection with the light baffles of FIG. 1, e.g., light absorbing VANTABLACK coating). The captured light 350 is then provided by the light guides 380 (e.g., optic fibers, etc.) to a photodiode, e.g., a circular photodiode 330 as illustrated in FIG. 3.

The structure thus may include a plurality or collection of optical fibers or guides 380 arranged to provide light from the circular arc directly to the photodiode 330. Alternatively, the light guides and the arc could be made of one unitary body so that light collection is not interrupted by the junctions that would inevitable product loss of signal and noise. The shape of such a unitary light collection device might resemble that of an onion with the fatter base of the onion surrounding the sample collection vial, and the apex of the onion being where the detector 330 sits. The inside of the onion would have a similar stray light absorber.

In another example, the components of the turbidimeter, e.g., the photodiode array and/or an arc element coupled with light guides, may be arranged to accommodate different sample holding structures, e.g., other than a standard cuvette or like sample vessel. By way of non-limiting example, an embodiment may be arranged as illustrated in FIG. 4.

Figure 4:
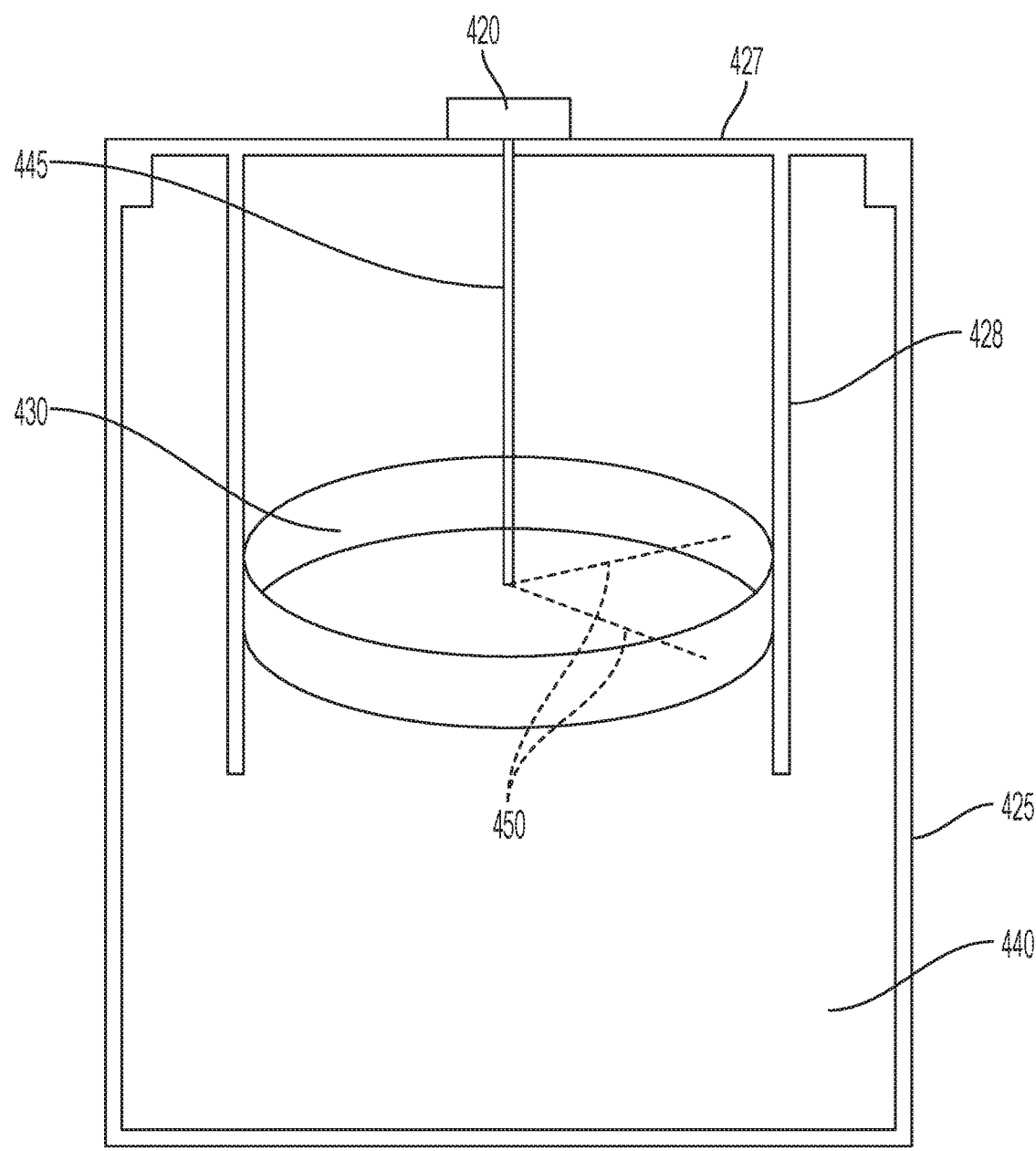
FIG. 4 illustrates another example turbidimeter.

In the illustrated example of FIG. 4, a cylindrical or arc element 430, e.g., including infrared photodiode(s), may be placed within a sample cell 425. As illustrated in FIG. 4, the cylindrical infrared photodiode 430 containing element is placed within the sample fluid 440, e.g., suspended above a light source 420, e.g., placed on a sample cell lid 427 of a sample cell 425. As illustrated in FIG. 4, the cylindrical detector 430 may be supported by one or more detector elements 428. As with the other example turbidimeters described herein, the example of FIG. 4 may include a photodiode array 430 or may be configured with light guide(s) such that light from the sample 440, and reflected by the sample (as indicated by 450) is directed to a detector 430 that processes the detected light to determine a sample concentration. It should be noted that light of other wavelengths may also be used, such as in the visible and near UV ranges.

Figure 5:
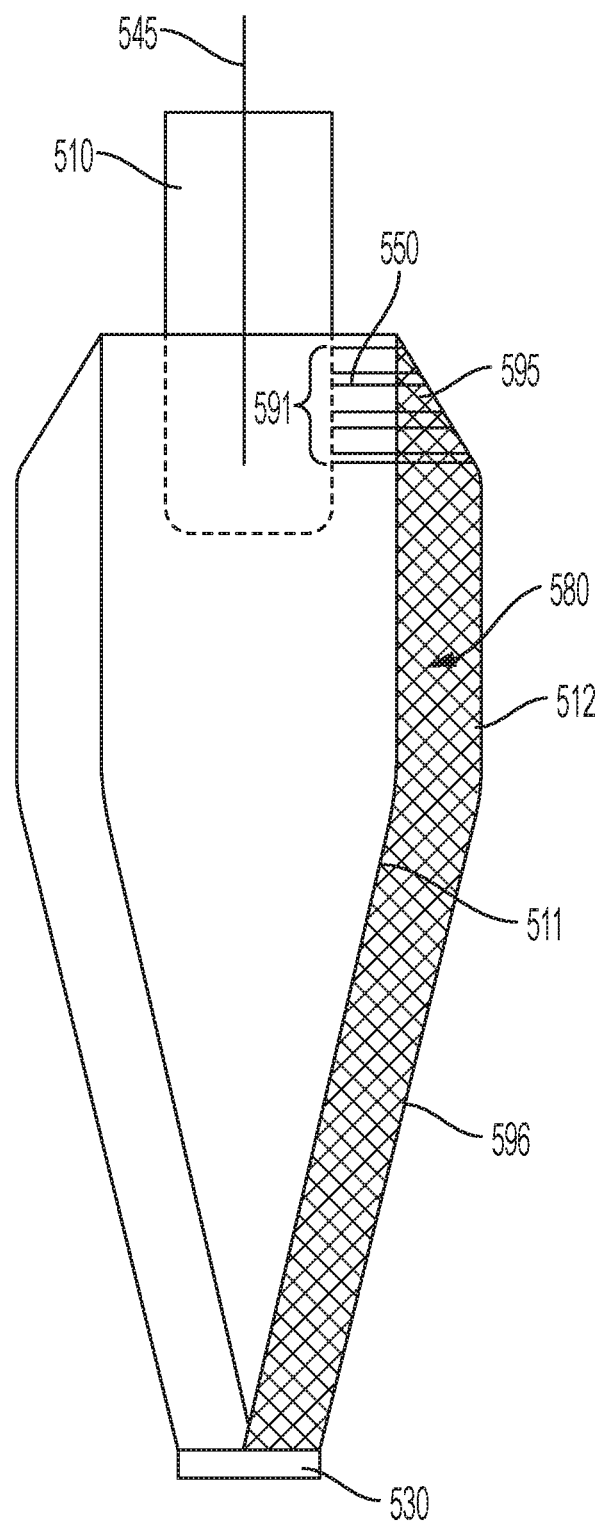
FIG. 5 illustrates another example turbidimeter.

In yet another embodiment depicted in FIG. 5, there is shown in cross-section a cone-shaped optical structure that utilizes the phenomenon of total internal reflection to channel and capture scattered light. In the embodiment illustrated in FIG. 5, the light 550 scattered from a sample in vial 510 is measured at the bottom or base end of the device, i.e., the measurement of turbidity of the media is carried out at a 90 degree angle to the incident light 545, with the light 550 being channeled by total internal reflection to a detector 530 that sits at the bottom of the device.

When incident light 545 is provided to the sample vial 510, which sits in an upper collar portion of the cone-shaped collector, the scattered radiation 550 at 90 degrees from incident, in an angular range of 360 degrees around the cuvette or vial 510, is collected by entry of the light 550 into a pathway 580 formed in the upper color portion of the cone shaped device. The scattered light 550 is collected in 360 degrees at an angle 90 degrees from the incident light 545, plus or minus an angular range (which is modifiable) effectively and safely with little effort on a small optical receiver or detector 530 that sits at the end of the device.

As shown in FIG. 5, an embodiment utilizes internal surfaces 511, 512 to form the pathway 580 around an outer periphery of the device. The internal surfaces 511, 512 are made of a material such that light 550 entering the pathway 580 is subject to total internal reflection, channeling it along the pathway 580 to the detector 530. The device, including internal surfaces 511, 512, may be produced by injection molding. The size of the device may be adapted to the measurement task (e.g., cuvette 510 size, device size, etc.). This example illustrated in FIG. 5 is only one example of a possible device configuration.

The device of FIG. 5 has at the top or collar portion an optically active aperture or light entryway 591 which receives the scattered radiation 550 from the sample vial 510 in 360 degrees. In an embodiment, angled surfaces or slants 595, 596 may be provided that reflect the light, e.g., via a coating appropriate surfaces of the slanted regions 595 or 596 with mirror or silvering material or coating. The angled surfaces 595, 596 may be chosen to functionally limit the amount of light reflected along the pathway 580 to the detector 530. For example, a slanted outer edge 595 in the structure dictates that only light at a certain height in the sample vial 510 is reflected along the light pathway 580. A specific opening angle (e.g., +/−2 degrees) may also be provided to the light entryway 591, e.g., such that this additional light satisfies the total reflection condition of the subsequent light guide structure 580. Only this light is guided in the structure's pathway 580 to the detector 530. All other light which does not satisfy this condition is suppressed as scattered light.

The useful light 550 enters the light pathway 580 and is internally reflected to detector 530 due to surfaces 511 and 512. At the end of the light pathway 580 the entire radiation is focused onto the detector 530. An example detector is a Si receiver.

To avoid reflection losses or total reflections at the end of the light pathway 580, the detector may be bonded with appropriate adhesives of suitable refractive index to direct the light onto the detector 530. When using other receivers or detectors, the size of the lower opening proximate to the detector 530 may be adjusted accordingly. For example, an adaptation of the end of the pathway 580 to accommodate a rectangular receiver or detector is possible in place of circular detector 530, as compared to the illustrated round opening. A rectangular receiver or detector may be dimmed according to the unused receiver surface. Also, the cuvette or sample vial 510 may be provided with a lens hood or appropriate covering structure (not illustrated in FIG. 5) so that the light pathway 580 and consequently the detector 530 receive no direct or unintended light.

Also, a mirror or like reflective coating of an inclined or slanted lower part 596 may be utilized. This may make the device simpler to design and construct, i.e., since reflection rather than total internal reflection is used for the lower portion. If such an arrangement is utilized, it must then be ensured that no stray light reaches the mirrored portion. As with other configurations, light blocking material or coatings may be utilized, e.g., mirror or silvering on exterior surfaces, such that stray light is not permitted a pathway to the detector 530.

The light from the photodiode/detector or photodiode array of any of the embodiments may be processed in a standard manner. The output from the photodiode or light pipes may be combined in a fashion that provides a summation of the signal. In the case of addressable photodiode arrays, photodiodes may be arranged to be summing, in circumferential groups providing the adjustment of collection angles. Thus, logic included with the turbidimeter or supporting components, e.g., a processor that executes instructions stored in a memory, may process the raw light data provided by the photodiodes such that the relative scattered light from the sample may be used to determine a concentration of particles in the sample.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, it is to be understood that the embodiments are not limited to those precise embodiments, and that various other changes and modifications may be affected therein by one skilled in the art without departing from the scope or spirit of the disclosure.

What is claimed is:

1. A turbidimeter comprising:
   a cone-shaped collector;
   the cone-shaped collector having a collar for receiving a cuvette;
   the collar including a light entryway that encircles the cuvette such that scattered light from the cuvette will enter the collar;
   a base end of the cone-shaped collector; and a detector element adjacent to the base end;
   the cone shaped collector comprising surfaces that form an internal light path that internally reflects the scattered light along a periphery of the cone-shaped collector from the cuvette to the base where the detector element sits.

2. The turbidimeter of claim 1, wherein said collar comprises a reflecting surface angled with respect to an impinging light axis.

3. The turbidimeter of claim 1, wherein said detector element comprises a photodiode.

4. The turbidimeter of claim 1, wherein said detector element comprises a Si receiver.

5. The turbidimeter of claim 1, wherein below said collar is a cone shaped portion of the cone-shaped collector having internal and external silvered surfaces.

6. The turbidimeter of claim 1, wherein said collar comprises light-absorbing baffle material to prevent unwanted scattered light from entering said light entryway.

7. The turbidimeter of claim 1, wherein the light entryway includes a specific opening angle of plus or minus 2 degrees.

* * * * *